(12) United States Patent
Barrelle et al.

(10) Patent No.: US 8,016,795 B2
(45) Date of Patent: Sep. 13, 2011

(54) DEVICE FOR ORAL ADMINISTRATION OF A MEDICINE

(75) Inventors: Laurent Barrelle, Saint-Nizier du Moucherotte (FR); Frederic Perot, Saint Paul de Varces (FR); Catherine Felix-Faure, Grenoble (FR)

(73) Assignee: Becton, Dickinson France S.A.S., Le Point de Claix (FR)

( * ) Notice: Subject to any disclaimer, the term of this patent is extended or adjusted under 35 U.S.C. 154(b) by 809 days.

(21) Appl. No.: 10/569,145

(22) PCT Filed: Aug. 12, 2004

(86) PCT No.: PCT/FR2004/002137
§ 371 (c)(1),
(2), (4) Date: Nov. 13, 2006

(87) PCT Pub. No.: WO2005/020875
PCT Pub. Date: Mar. 10, 2005

(65) Prior Publication Data
US 2007/0083164 A1 Apr. 12, 2007

(30) Foreign Application Priority Data
Aug. 21, 2003 (FR) .................................. 03 10079

(51) Int. Cl.
*A61M 5/00* (2006.01)
(52) U.S. Cl. ...................................... 604/187
(58) Field of Classification Search ............ 604/82, 604/187, 227
See application file for complete search history.

(56) References Cited

U.S. PATENT DOCUMENTS

| | | | |
|---|---|---|---|
| 3,572,337 A * | 3/1971 | Schunk ........................ 604/77 |
| 4,393,864 A | 7/1983 | Galkin et al. |
| 4,465,785 A | 8/1984 | Kelland |
| 4,516,967 A | 5/1985 | Kopfer |
| 4,540,405 A | 9/1985 | Miller et al. |
| 5,047,021 A * | 9/1991 | Utterberg .................. 604/533 |
| 5,069,225 A * | 12/1991 | Okamura .................... 600/578 |
| 5,244,122 A | 9/1993 | Botts |
| 5,330,450 A * | 7/1994 | Lopez ........................ 604/533 |
| 5,374,264 A * | 12/1994 | Wadsworth, Jr. .......... 604/414 |
| 5,417,660 A | 5/1995 | Martin |
| 5,624,405 A * | 4/1997 | Futagawa et al. ......... 604/199 |
| 5,702,019 A * | 12/1997 | Grimard .................... 215/301 |
| 5,876,379 A | 3/1999 | Blatt et al. |
| 5,893,397 A | 4/1999 | Peterson et al. |

(Continued)

FOREIGN PATENT DOCUMENTS
EP 0764450 A 3/1997
(Continued)

*Primary Examiner* — Nicholas D Lucchesi
*Assistant Examiner* — Weng Lee
(74) *Attorney, Agent, or Firm* — Cozen O'Connor

(57) ABSTRACT

An assembly for oral administration of a medicinal product to be reconstituted from an active principle in dry or liquid form and from a diluent, A device including a prefilled syringe with said diluent, able by itself to receive a parenteral injection member is provided. A support including a body of elongate form is fastened to the syringe, the support includes a device for fixing to the syringe and, at its distal end a device for preventing the connecting of the needle to the tip of the syringe. A bottle including the active principle and a system for transferring the diluent to the active principle, then the reconstituted medicinal product from the bottle to the syringe, the transfer system being separate from the support.

23 Claims, 13 Drawing Sheets

U.S. PATENT DOCUMENTS

Figure 1:
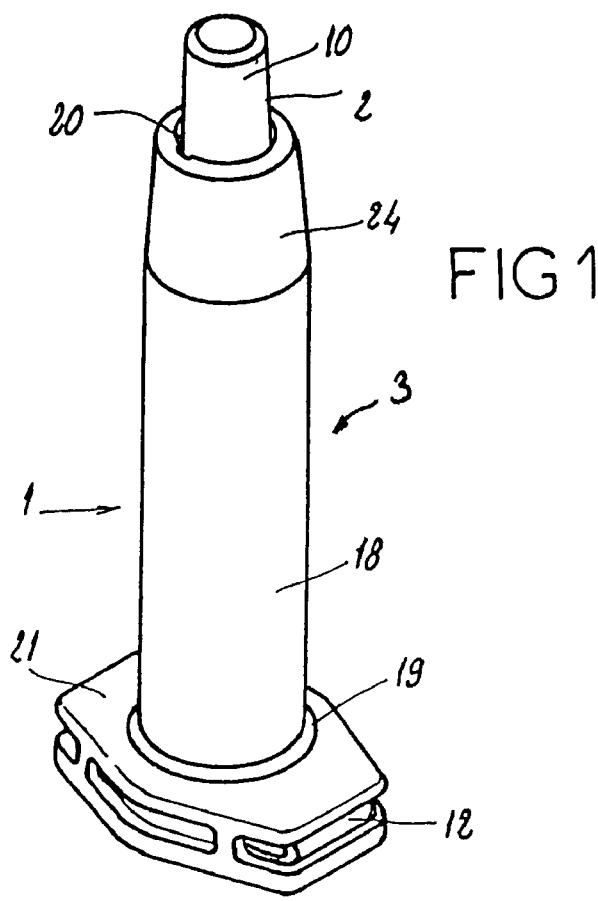

| | | | |
|---|---|---|---|
| 5,925,032 A * | 7/1999 | Clements | 606/1 |
| 5,951,526 A | 9/1999 | Korisch et al. | |
| 6,344,032 B1 | 2/2002 | Perez et al. | |
| 6,729,370 B2 * | 5/2004 | Norton et al. | 141/329 |
| 2003/0171719 A1 * | 9/2003 | Veillon et al. | 604/187 |
| 2004/0167476 A1 * | 8/2004 | Westbye | 604/192 |

FOREIGN PATENT DOCUMENTS

| | | |
|---|---|---|
| EP | 1129786 | 5/2001 |
| FR | 2653667 A | 5/1991 |
| FR | 2821561 A | 5/2003 |

* cited by examiner

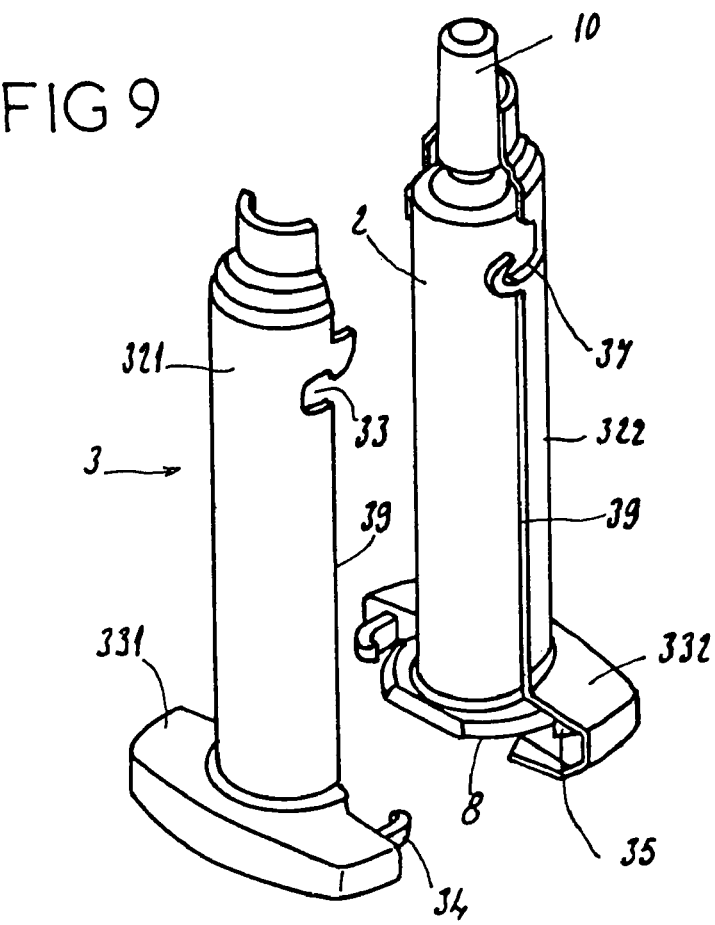
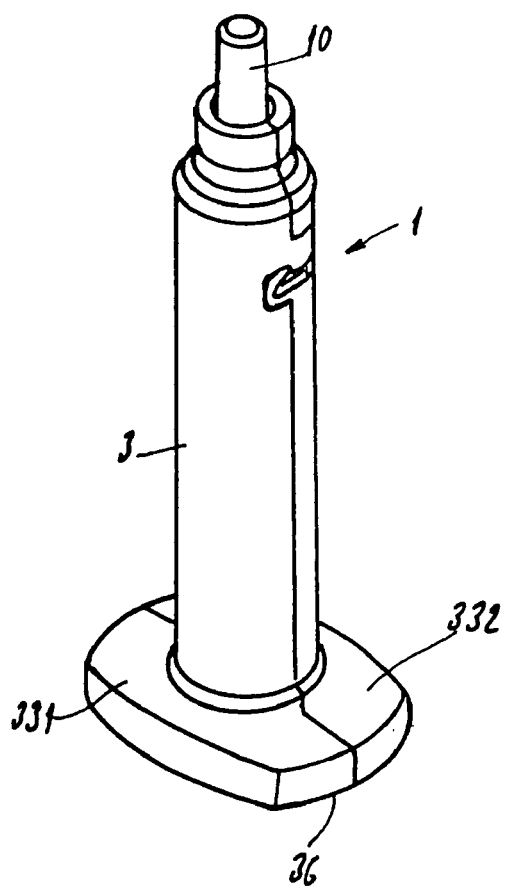

DEVICE FOR ORAL ADMINISTRATION OF A MEDICINE

PRIORITY CLAIM

This is a U.S. national stage of application No. PCT/FR04/02137, filed on Aug. 12, 2004. Priority is claimed on that application and on the following application: FR 0310079 Country: France, filed: Aug. 21, 2003.

The present invention relates to an assembly for the oral administration of a product, for example medicinal, to be reconstituted from an active principle in dry or liquid form, comprising a bottle comprising said active principle, a transfer system and a device comprising a support and a syringe.

The use of a syringe for the oral administration of medicines is known. This method proves particularly practical and advantageous in children and the elderly. In a conventional manner, such a syringe comprises a tubular body, a tip and a plunger. The medicine, contained in a separate bottle, is sucked into the body of the syringe by withdrawing the plunger towards the proximal end of the syringe and then injected into the mouth of the patient by pushing the plunger towards the distal end of the syringe.

However, in certain cases, it is necessary for the syringe to be prefilled. For example, the syringe may contain a diluent of an active principle in dry form, such as a powder or a lyophilisate, or in liquid form. In this case, the syringe must firstly be connected, preferably by its tip, to the bottle containing the for example powder active principle, by means of a transfer system, then the medicinal product is reconstituted by mixing the said active principle with the diluent already present in the syringe. The medicinal product can then be introduced into the mouth of the patient.

The syringe can also be prefilled directly with a medicine in liquid form.

In the case of certain products, it is particularly important for the contents of the syringe, be they the medicine, the diluent or the reconstituted medicinal product, not to be injectable into the patient parenterally, for example subcutaneously or intravenously by means of a parenteral injection member, such as a needle, a catheter or a perfusion line. Indeed, such an injection could be fatal for the patient.

It is also beneficial from a practical point of view to be able to use standard prefilled syringes for oral administration of medicinal product.

Moreover, when the syringe used is a glass syringe, it is important, especially when the patient is a child, that this syringe does not come in contact with the child's mouth for instance, or with any other body part, that it could hurt in case of breakage. In this case, it is also important that the syringe be protected from collisions.

Thus, the need exists for a safe device for oral administration of medicinal product using prefilled syringes, in particular standard prefilled syringes, for example made out of glass, permitting on the one hand oral administration of the product and precluding on the other hand parenteral administration of this same product. The assembly comprising such a device, the bottle comprising the active principle in dry or liquid form, and the transfer system, must thus preclude parenteral injection of all product while at the same time allow the connection of the transfer system to the syringe.

The document WO 94/13347 describes a device comprising in combination a prefilled syringe and a support that can be fixed to the syringe with a view to preventing the contamination of the latter during its use. This device does not preclude the connecting of a parenteral injection member to the tip of the syringe and therefore also does not preclude the parenteral administration of the product contained in the syringe.

The document U.S. Pat. No. 4,516,967 describes an assembly for the parenteral administration of a medicinal product to be reconstituted from an active principle in dry form and from a diluent comprising a prefilled syringe provided with a needle, a bottle comprising the active principle in dry form and a transfer system under the shape of a plastic tube connecting the syringe to the bottle. In U.S. Pat. No. 4,516,967, once the medicine is reconstituted, and once the bottle and the transfer system are removed, the syringe provided with the needle is ready to be used for a parenteral injection.

In a conventional manner, a parenteral injection member is provided furnished with a connection base. Thus, conventionally, a removable injection needle consists of a generally metallic tubular needle fixed on a base, for example made of plastic in the form of a hollow cone, intended to come into contact with the tip of the syringe, which is itself conical, such as the so-called "Luer" assembly known per se. This hollow cone is generally furnished with two flanges at its bottom so as to fit a tapped part of the parenteral injection member so as to ensure the maintaining of leak-free contact of the base on the tip.

To preclude the use by parenteral route of a syringe in the desired oral application, it is necessary to prevent any potential connecting of a parenteral injection member, in particular of the "Luer" type, at the level of the tip of the syringe. In particular, connecting of the member by contacting and/or screwing of its base must be impossible. Anyway, the connection of the transfer system to the syringe must remain possible.

The present invention aims to remedy these problems by providing a safe assembly for oral administration of medicinal product allowing the use of standard prefilled syringes in the reconstitution of a medicine from an active principle under dry or liquid form via connection of the transfer system to the syringe, then the oral administration of the product while precluding on the other hand parenteral administration of this same product.

A subject of the present invention is an assembly for oral administration of a medicinal product to be reconstituted from an active principle in dry or liquid form and from a diluent, characterized in that it comprises:
  i) a device comprising:
     a prefilled syringe with said diluent, furnished at its distal end with a tip and at its proximal end with a collar, this syringe being able by itself to receive a parenteral injection member,
     a support comprising a body of elongate form which is fastened to the syringe, preferably surrounding it, the said support being open at its distal end and at its proximal end, the said support comprising at its proximal end means for fixing to the syringe,
  and, at its distal end, at least one means for preventing the connecting of the parenteral injection member to the tip of the syringe,
  ii) a bottle comprising the active principle in dry or liquid form and
  iii) a system for transferring the diluent to the active principle, then the reconstituted medicinal product from the bottle to the syringe,
said transfer system being separate from the support.

Thus, by virtue of the assembly according to the invention, it is possible to use prefilled syringes, for example standard prefilled syringes made out of glass, for oral administration of product without any risk of the product contained in the syringe being administered parenterally, this being so throughout the syringe handling time. Moreover, because the support surrounds the syringe and because it is fixed on the syringe during all the time of the handling, and in particular after the reconstitution of the medicine and the removal of the transfer system, there is no risk that glass, for instance in the case of a syringe made out of glass, comes in contact with the mouth or the body of the patient. Also, if the syringe is made out of glass, it is protected from collisions and therefore from breakage risks by the support.

For example, in the case of a medicinal product requiring reconstitution, the device of the assembly according to the invention renders parenteral injection impossible during all the syringe handling steps, that is to say during the step of connecting the syringe to the bottle comprising the active principle in dry or liquid form, then during the step of reconstituting the medicinal product and finally during the actual step of administering the product into the mouth of the patient, while at the same time allowing the connection of the transfer system to the syringe for the reconstitution of the medicinal product.

Likewise, in the case of a syringe directly prefilled with a medicine, the parenteral injection of this medicine is also rendered impossible by virtue of the device of the assembly according to the invention. The device of the assembly according to the invention is thus made entirely safe. By virtue of this device, the undesired parenteral administration of the product contained in the syringe is not possible.

This assembly finds an application in particular in respect of the oral administration of medicinal products taking the form of two products to be mixed: a first product, for the example in the form of powder or lyophilisate, or in the form of a liquid, is contained in a bottle and a second product, for example a diluent is contained in a syringe thus prefilled. Thus, throughout the preparation of the medicinal product and its administration to the patient, the risk of injecting the said product by a route other than oral is absent.

In the present patent application, the expression distal end of a piece is understood to mean the end furthest from the user of the device and the expression proximal end is understood to mean the end closest to the user of the device.

In the present patent application, the expression "parenteral injection member" is understood to mean any member allowing the subcutaneous or intramuscular or intravenous injection of a product, such as a needle, a catheter, a perfusion line or any other system the connecting of which is as described for example in ISO standard 594-2.

The syringe of the assembly according to the invention is generally a conventional prefilled syringe comprising in a general manner a substantially tubular body, a tip and a collar.

The collar of the syringe of the device according to the invention can be of variable shape. It may be circular or on the contrary formed of radial parts facing one another. It may be merely a simple rim, in particular in the case where the syringe is a carpule.

The syringe may be prefilled with a medicine in liquid form or with an active principle diluent for example.

Advantageously, the support is fixed definitively to the syringe. It is thus not possible for the user to separate the support from the syringe and to use the syringe for a parenteral injection. The device is thus made safe.

Preferably, the support is fixed to the syringe by bonding, welding, clipping, snap-fastening, crimping or hot deformation.

In a preferred form of embodiment of the invention, the means for fixing the support to the syringe take the form of a washer comprising a transverse platform and a rim running in the proximal direction and able to deform and to clip to the collar of the syringe.

In a preferred form of embodiment of the invention, the means for preventing the connecting of the parenteral injection member to the tip of the syringe take the form of a distal part, situated at the distal end of the support, the free end of the said distal part exhibiting an opening, preferably axial, whose internal diameter is strictly less than the external diameter of the base of the said parenteral injection member.

The expression internal diameter is understood, within the sense of the present patent application, to mean the diameter of the circle inscribed within the cross section of the axial opening of the said distal part. This cross section may be of circular or substantially circular form with indents. In another form of embodiment of the invention, this cross section has a polygonal shape. Preferably also, this internal diameter is less than or equal to 7.70 mm. Preferably also, the distance between the longitudinal axis of the tip of the syringe and the point of the perimeter of the opening closest to this axis is less than or equal to 3.85 mm.

The expression external diameter is understood, within the sense of the present patent application, to mean the diameter of the circle within which is inscribed the largest cross section of the base of the parenteral injection member.

In one form of embodiment of the invention, the distal part is a hollow tapered portion converging in the distal direction.

In another form of embodiment of the invention, the distal part is a hollow cylinder.

In one form of embodiment of the invention, the body of the syringe is furnished on its external surface with an annular piece, for example of plastic, onto which the support is fixed.

Preferably, the annular piece is a ring with plunger anti-withdrawal effect. This ring prevents the plunger from coming out of the syringe. Such rings are described in documents EP 0 764 450, WO 94/26334 and U.S. Pat. No. 5,803,918.

In a preferred form of embodiment of the invention, the support is furnished at its proximal end with a ring with plunger anti-withdrawal effect.

In another form of embodiment of the invention, the support is furnished at its distal end with a cap linked to the support by at least one breakable bridge. This breakable bridge serves as tamper-proofing element. In combination with the plunger anti-withdrawal ring, the device is thus made entirely safe from the tamper-proofing point of view.

Preferably, the support of the device of the assembly of the invention is obtained by moulding a thermoplastic material, such as polyethylene, polycarbonate or polypropylene.

In one form of embodiment of the invention, the body of the support comprises at least one longitudinal window. This window allows observation of the contents of the syringe.

In another form of embodiment of the invention, the support is formed of two longitudinal parts fixed together. Preferably, each longitudinal part is obtained by moulding a thermoplastic material, such as polyethylene, polycarbonate or polypropylene.

Preferably, the two longitudinal parts are fixed together by bonding, welding, clipping, snap-fastening, crimping or hot deformation, with the aid of a hinge or through a combination of these means.

Advantageously, the support is furnished with a transverse skirt preventing the device from penetrating too far into the mouth of the patient. There is thus no risk of injuring the latter.

Advantageously, the syringe is made of glass.

Another subject of the present invention pertains to the use of a device comprising:

a prefilled syringe with a diluent, furnished at its distal end with a tip and at its proximal end with a collar, this syringe being able by itself to receive a parenteral injection member, a support comprising a body of elongate form which is fastened and fixed in a definitive way to the syringe, preferably surrounding it, the said support being open at its distal end and at its proximal end, the said support comprising at its proximal end means for fixing to the syringe, and, at its distal end, at least one means for preventing the connecting of the parenteral injection member to the tip of the syringe, to render parenteral injection of the diluent or of the reconstituted medicinal product impossible, in an assembly for oral administration of a medicinal product to be reconstituted from an active principle in dry or liquid form contained in a bottle and the diluent and comprising a transfer system (52), during all the syringe handling steps, while allowing the connection of the transfer system to the syringe.

In one form of embodiment of the invention, the transfer system comprises at its distal end an extreme part able to connect to the tip of the syringe once the support has been fixed to the said syringe.

In one form of embodiment of the invention, the extreme part of the transfer system comprises means for making safe the transfer system on the device. The safety of the assembly is thus reinforced.

In a preferred embodiment of the invention, the means for preventing the connecting of the parenteral injection member to the tip of the syringe takes the form of a distal part, situated at the distal end of the support, the free end of the said distal part exhibiting an axial opening comprising at least one notch, preferably at least two notches, more preferably two notches, the securing means of the transfer system taking the form of at least one lug, preferably at least two lugs, more preferably two lugs, able to cooperate with the notch(es) of the distal part of the support. Preferably, the axial opening comprises two notches and the securing means take the form of two lugs, these two lugs being offset in the axial direction or in an angular manner or else according to a combination of these two modes. In this way, an unsuitable bottle, that could contain a dangerous or unwished substance, can not be used in the so secured assembly of the invention.

In one form of embodiment of the invention, the transfer system is definitively crimped to the bottle. In this case, the transfer system is irremovable and is furnished with a mobile internal needle activated upon connecting the transfer system with the syringe. Thus, the user may not use a wrong bottle. Such systems are described in the documents U.S. Pat. No. 5,925,029, U.S. Pat. No. 6,003,566, U.S. Pat. No. 6,090,093, U.S. Pat. No. 6,189,580, U.S. Pat. No. 6,213,994, U.S. Pat. No. 6,378,576, U.S. Pat. No. 6,378,714 and U.S. Pat. No. 6,382,442.

For the proper understanding thereof, the invention is described hereinbelow with reference to the appended diagrammatic drawing, representing, by way of nonlimiting example, preferred forms of embodiment of the device to which it relates.

Figure 3:
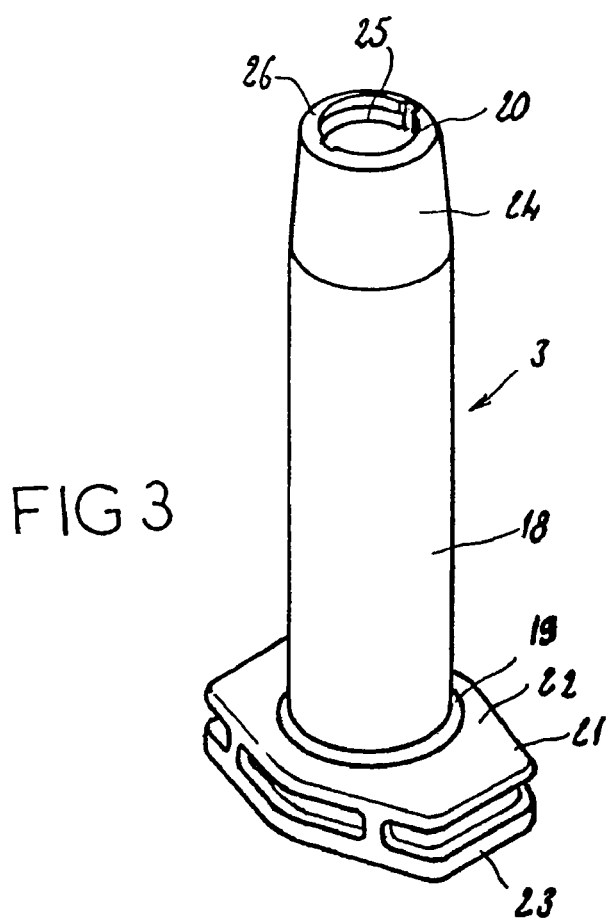
Figure 2:
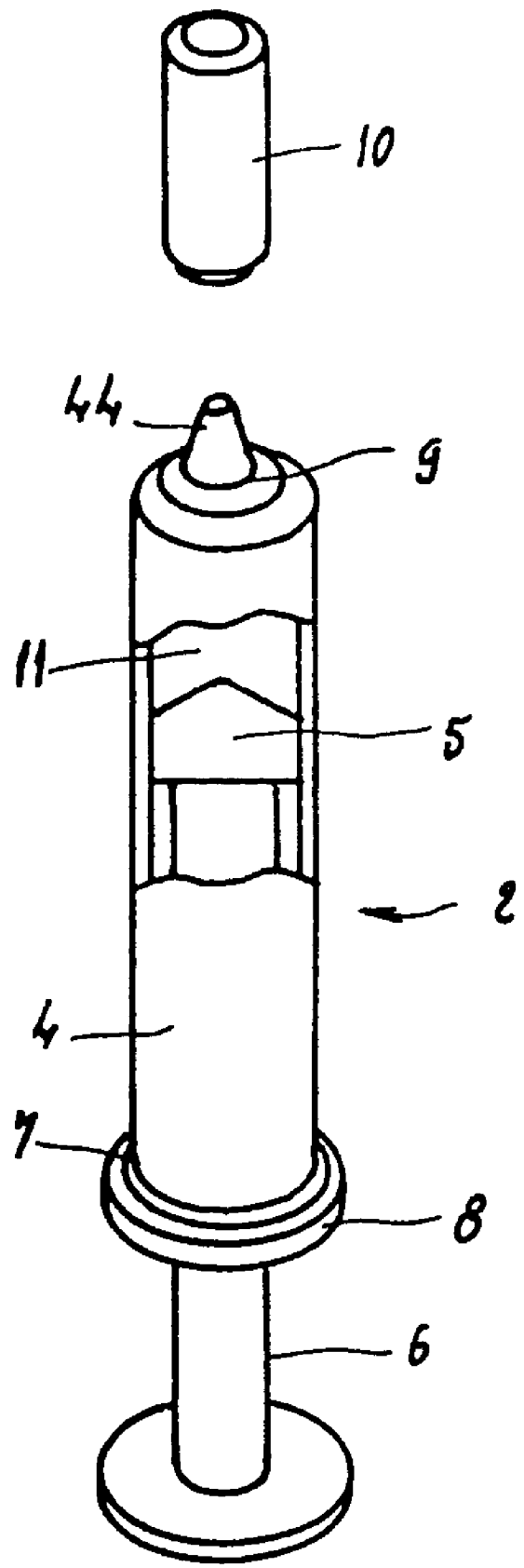
Figure 4:
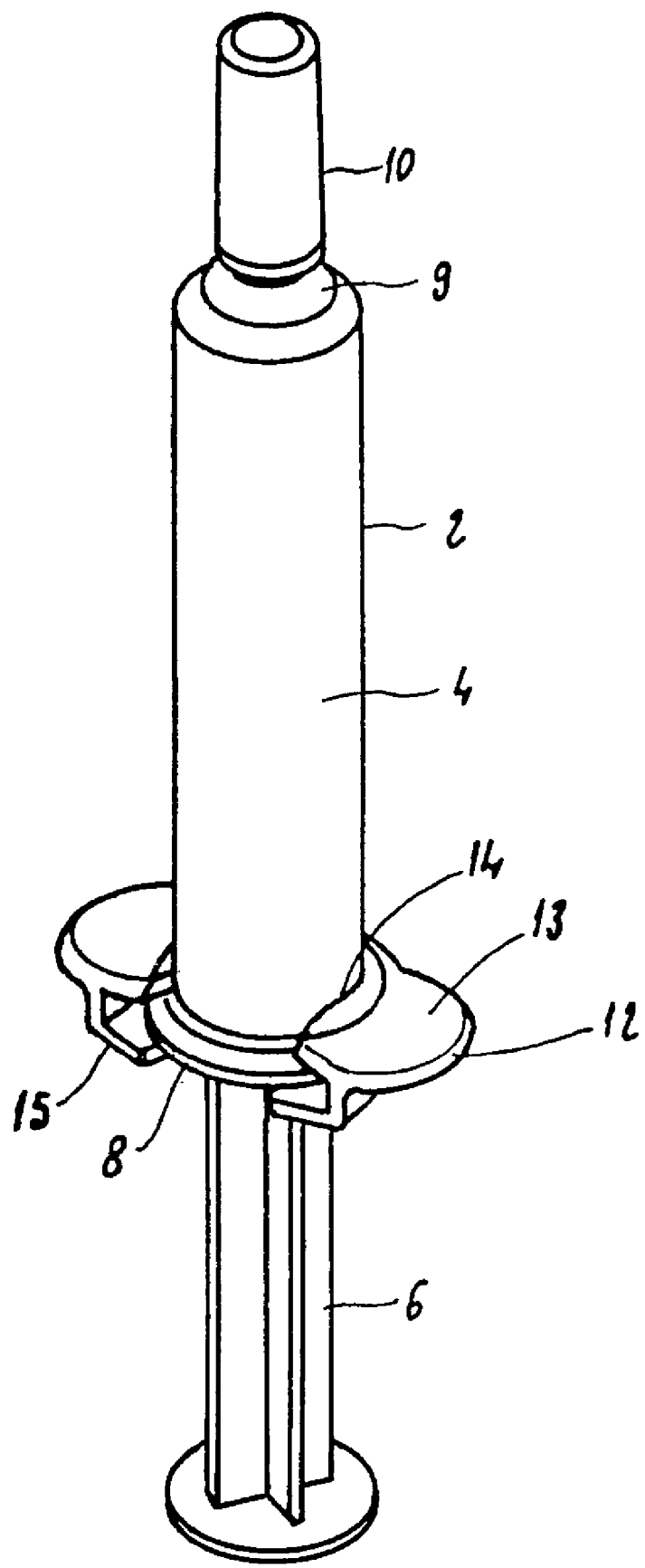
Figure 5:
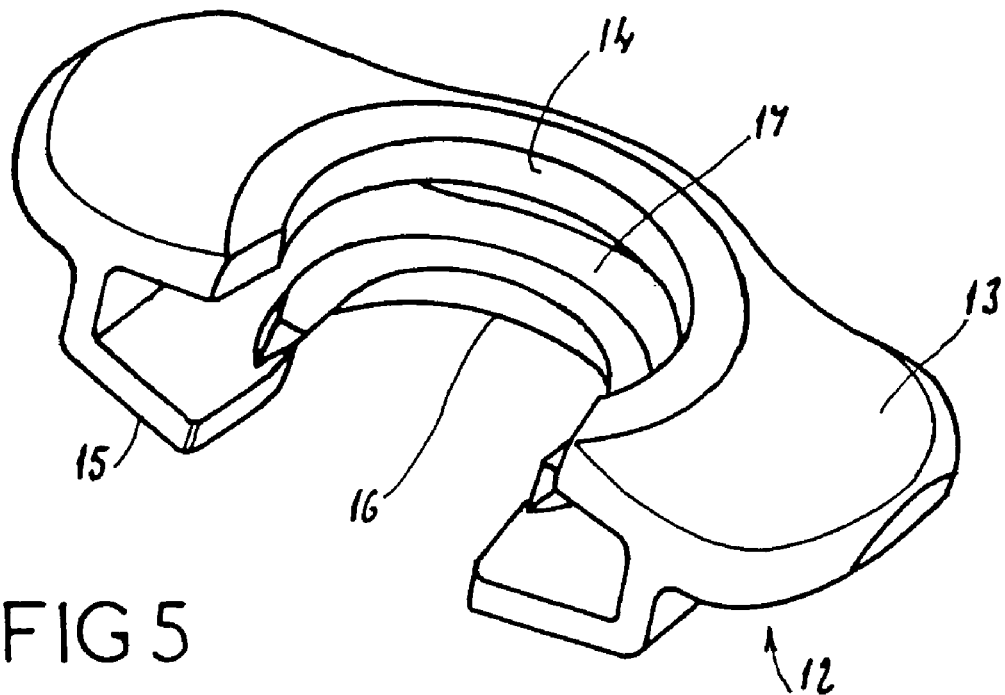
Figure 6:
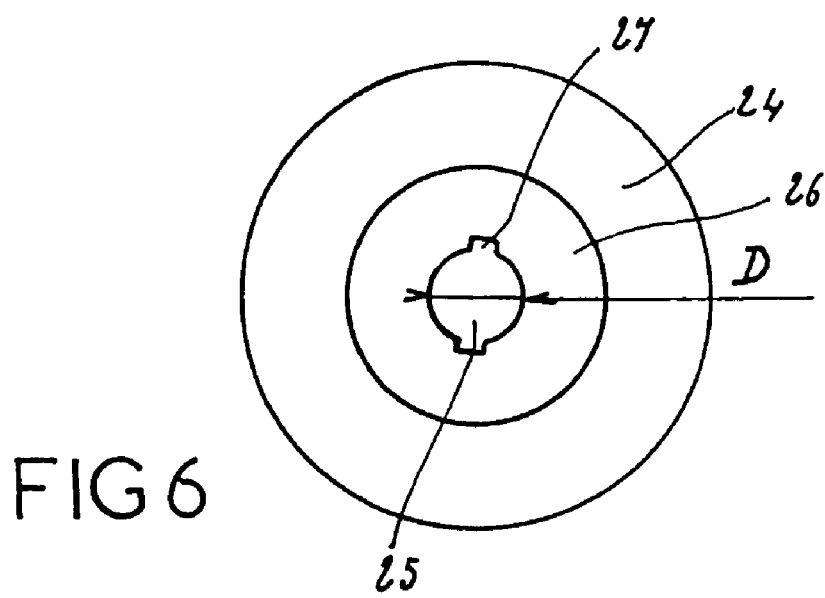
Figure 7:
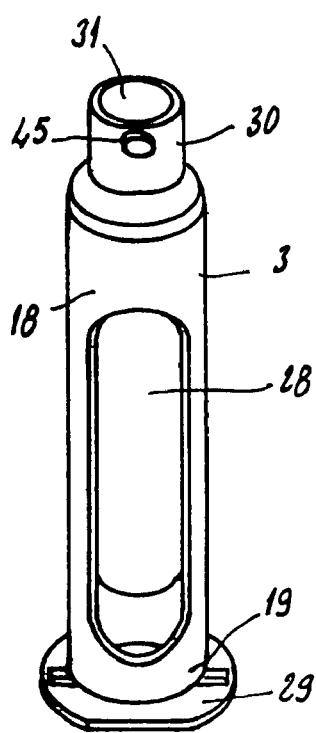
Figure 8:
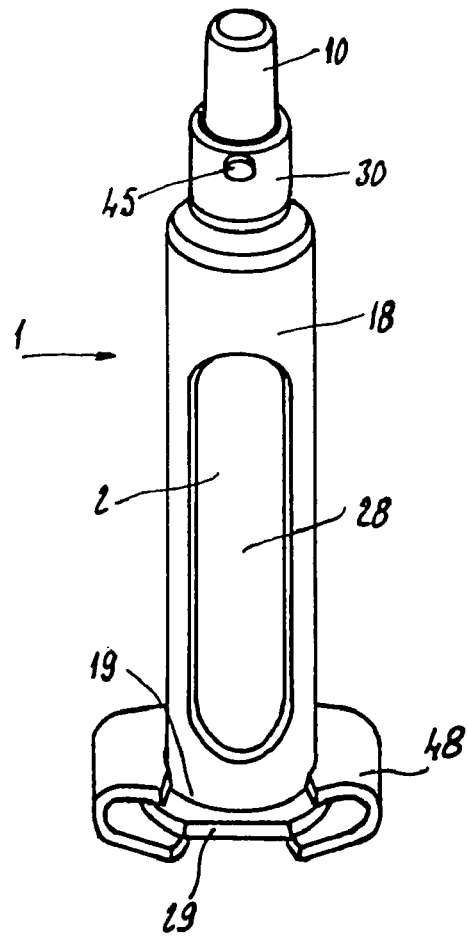
Figure 11:
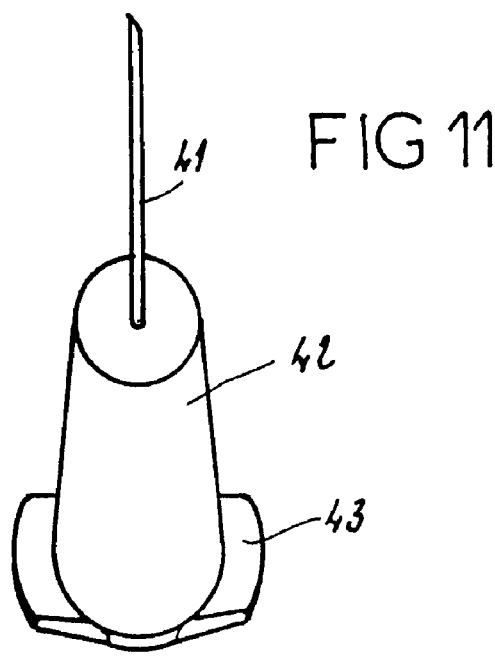
Figure 12:
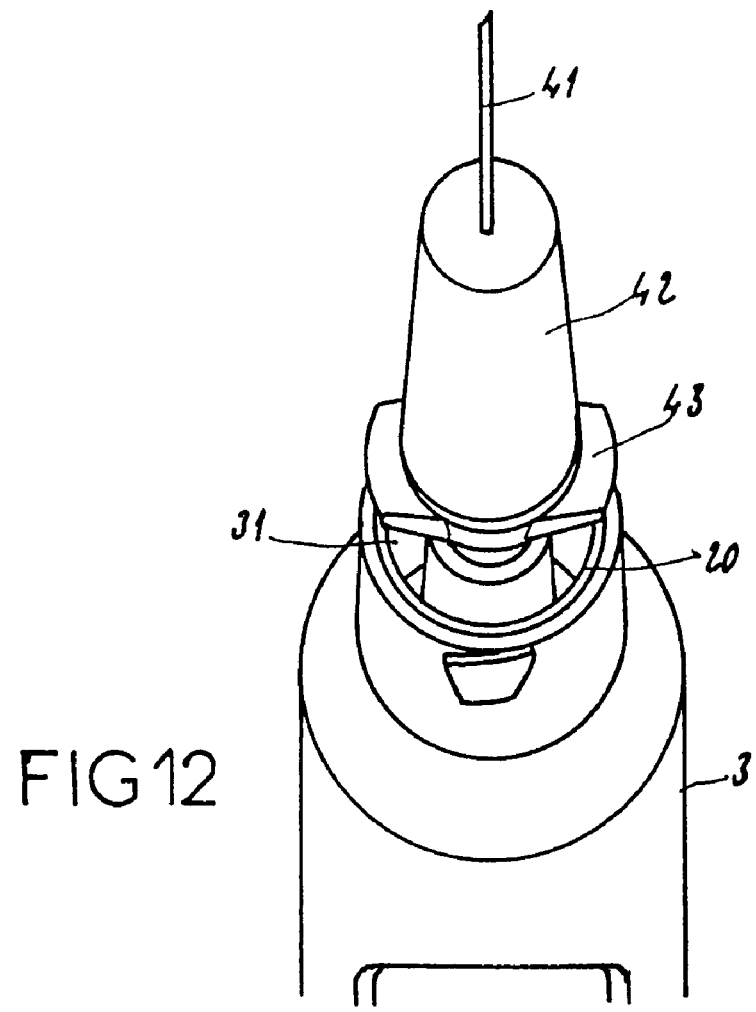
Figure 13:
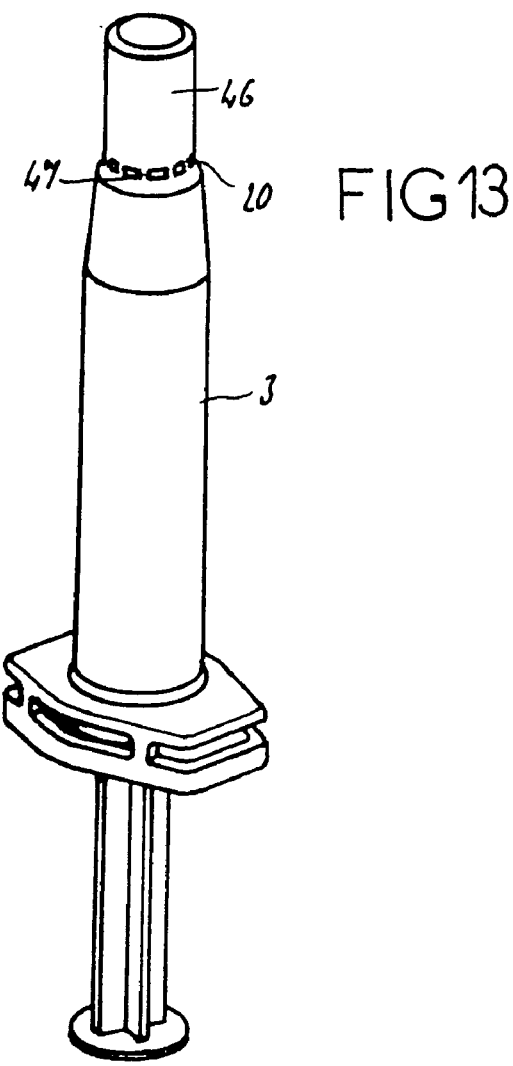
Figure 14:
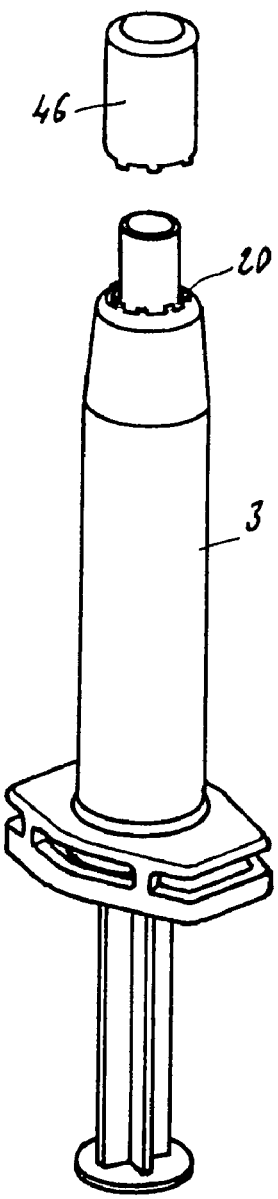
Figure 15:
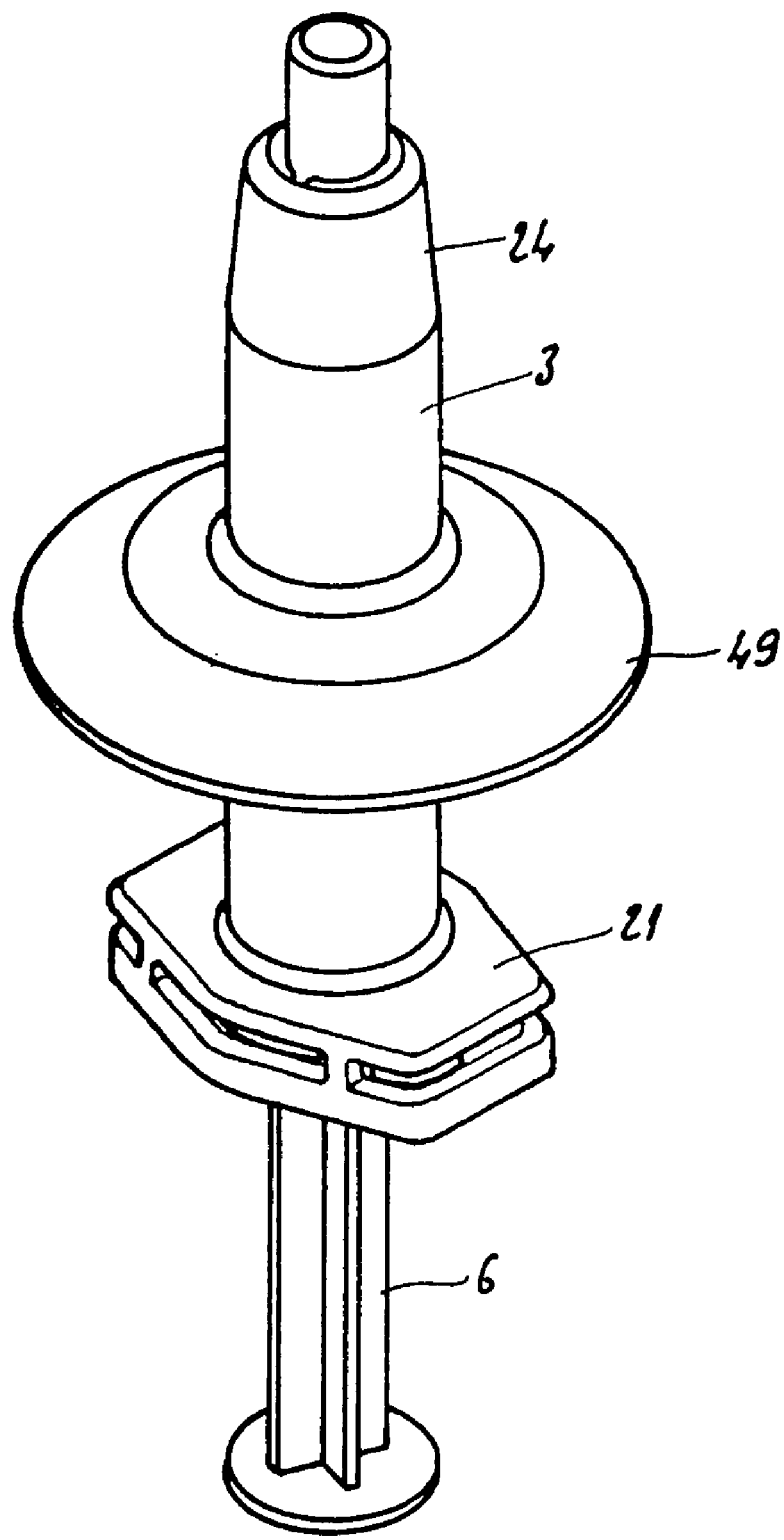
Figure 16:
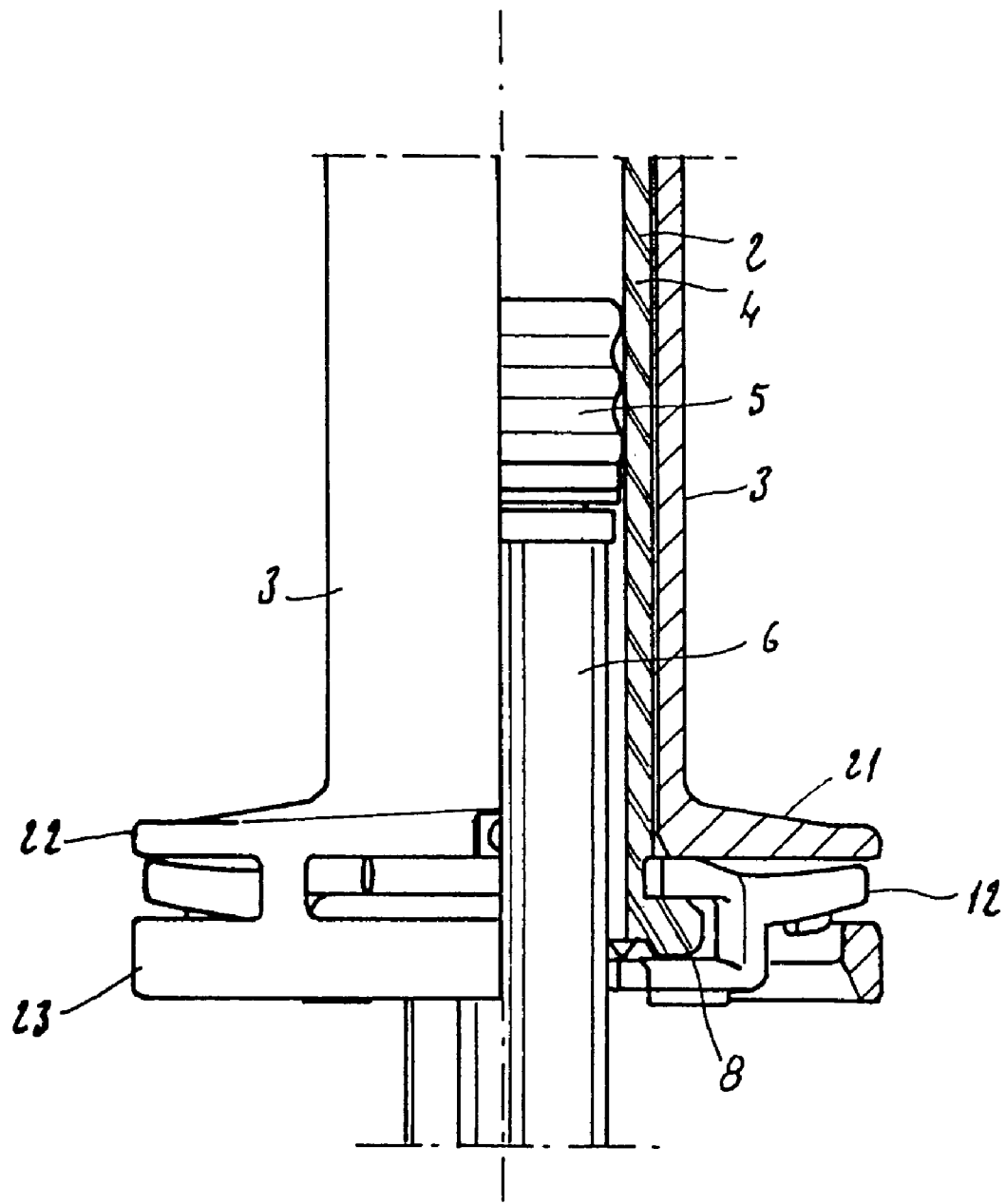
Figure 17:
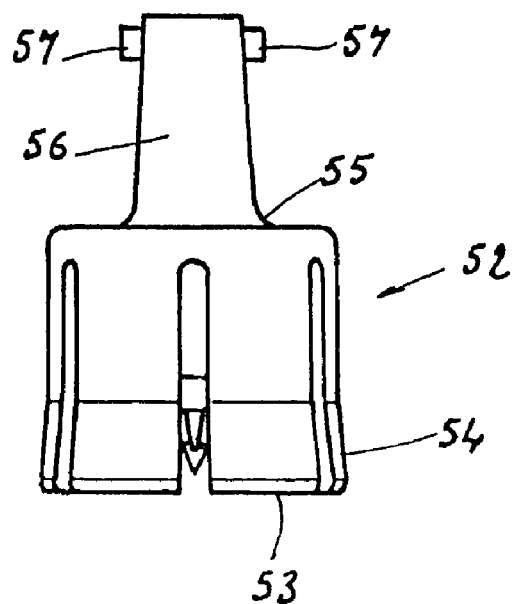
Figure 18:
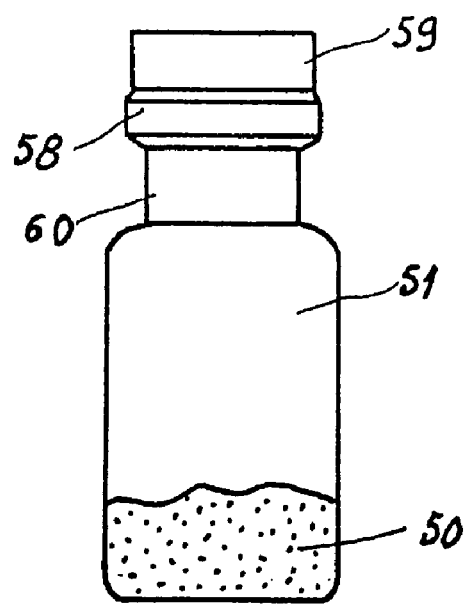
Figure 19:
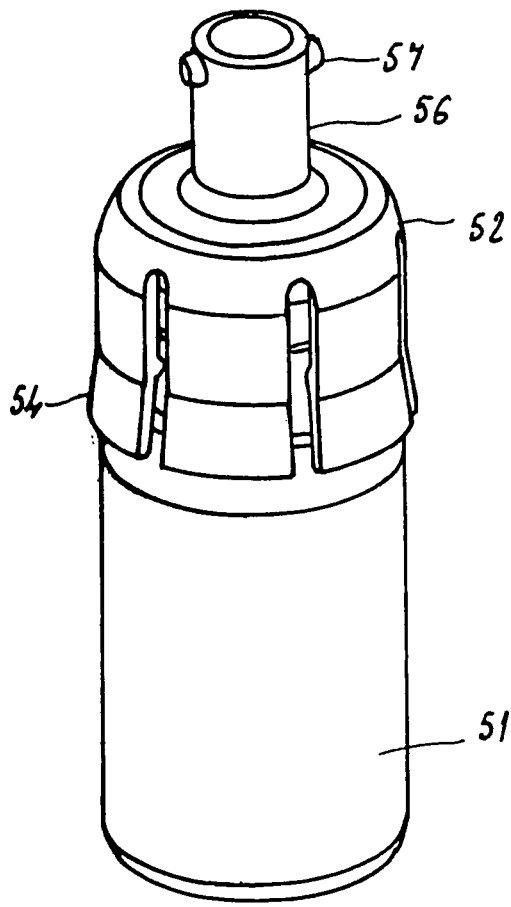
Figure 22:
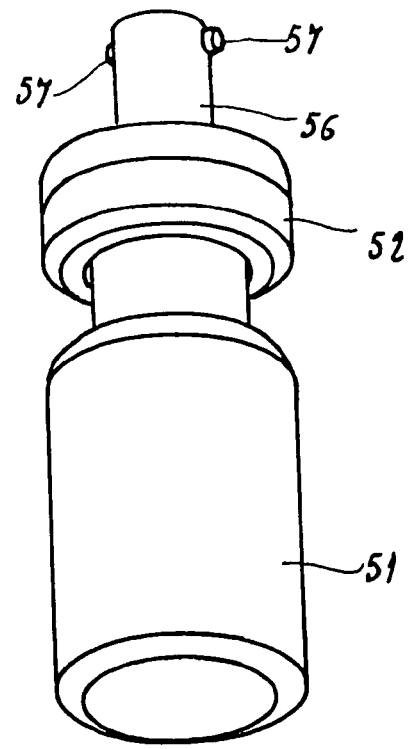
Figure 20:
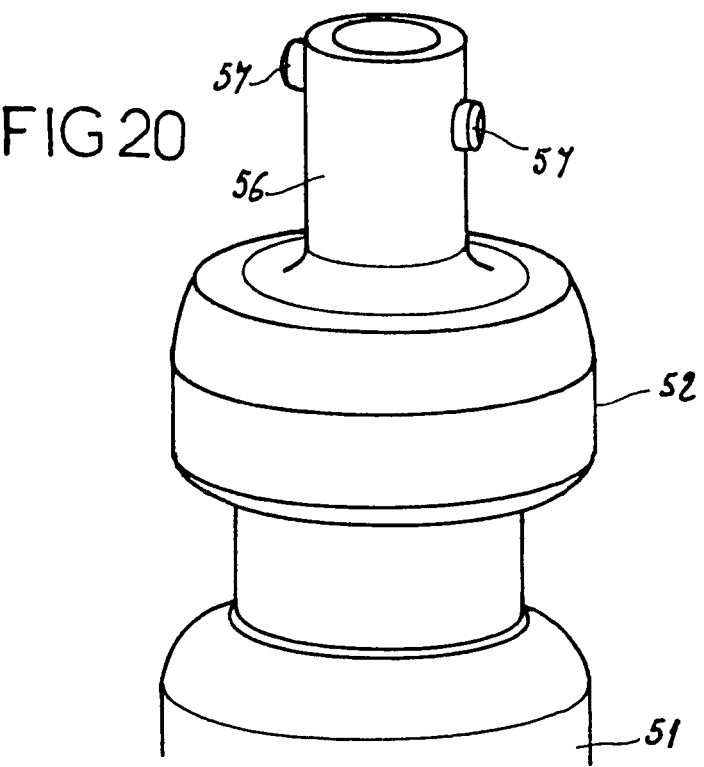
Figure 21:
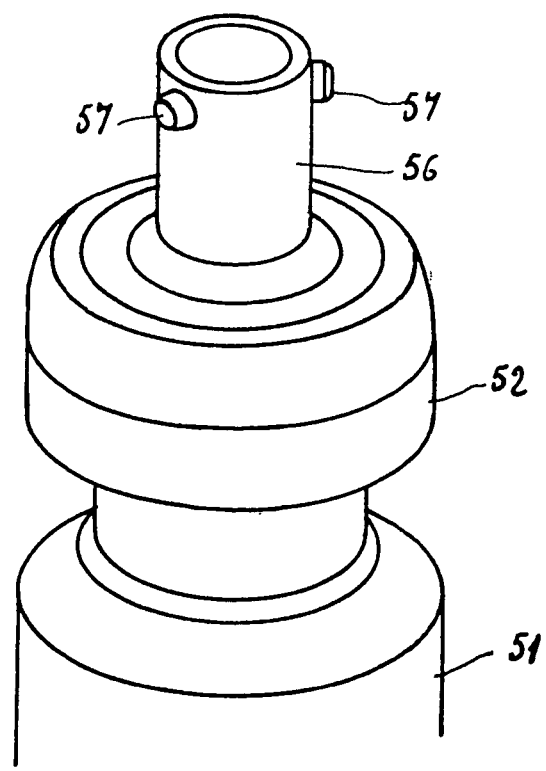

FIG. 1 is a perspective view of a device of an assembly according to the invention showing a prefilled syringe installed in a support, FIG. 2 is a perspective view of the prefilled syringe of the device according to FIG. 1, FIG. 3 is a perspective view of the support of the device according to FIG. 1, FIG. 4 is a perspective view of the syringe of the device according to FIG. 1, furnished with a ring with plunger anti-withdrawal effect, FIG. 5 is a perspective view of the ring with anti-withdrawal effect of the plunger of the syringe of the device according to FIG. 4, FIG. 6 is a view from above of the conical part of the distal end of the support according to FIG. 3, FIG. 7 is a perspective view of a support of a variant of a device of an assembly according to the invention, FIG. 8 is a perspective view of a variant of the device comprising a support according to FIG. 7, FIG. 9 is an exploded perspective view of another variant of a device of the assembly according to the invention, FIG. 10 is a perspective view of the device according to FIG. 9 once the support has been fixed to the syringe, FIG. 11 is a perspective view of a parenteral injection member, FIG. 12 is a perspective view illustrating the impossibility of connecting a parenteral injection member to a syringe installed in a support according to a device of the assembly of the invention, FIGS. 13 and 14 are perspective views of another variant of the device according to the invention, FIG. 15 is a perspective view of another variant of a device of an assembly according to the invention, FIG. 16 is a sectional view of a part of the device according to FIG. 1, FIG. 17 is a side view of a transfer system allowing the transfer of a diluent and of an active principle between the bottle and the syringe of the assembly according to the invention, FIG. 18 is a sectional view of a bottle containing an active principle to be transferred into the syringe of the device of the assembly according to the invention with the aid of the transfer system of FIG. 17, FIG. 19 is a perspective view of the transfer system of FIG. 17, installed on the bottle of FIG. 18, FIG. 20 is a perspective view of a variant of FIG. 19 in which the transfer system is crimped to the bottle, FIGS. 21 and 22 are perspective views showing the means of making safe the transfer system on the device of the assembly according to the invention.

The parts or elements of the device that are shown in FIGS. 1 to 22, which appear in an identical or similar manner in the various alternative embodiments, will be labelled by the same numerical references and will therefore not be described again.

FIG. 1 represents a device 1 for oral administration of a medicinal product comprising a syringe 2 and a support 3 fastened to this syringe 2 and surrounding it. As represented in FIG. 2, the syringe 2 is a syringe prefilled with a liquid 11, comprising at its distal end 9, a tip 44 and at its proximal end 7, a collar 8. This syringe 2 is able by itself to receive a parenteral injection member 41 such as for example represented in FIG. 11. Also represented in FIGS. 1 and 2 is a cap 10 for stoppering and protecting the tip 44. The syringe 2 comprises in a conventional manner a body 4 of tubular form and a plunger consisting of a plunger seal 5 and of a plunger rod 6. In FIG. 1, the syringe 2 is entirely covered by the support 3. Only the cap 10 of the tip 44 of the syringe 2 protrudes from the device 1. The syringe 2, in the configuration according to FIG. 1, can no longer be connected to a parenteral injection member.

Represented in FIG. 3 is the support 3 of the device 1 of FIG. 1. This support 3 comprises a body 18 of elongate shape able to receive the syringe 2. This body 18 is hollow, preferably cylindrical and its internal surface has a diameter suitable for receiving the syringe 2. This body 18 is open at its proximal end 19, to receive the syringe 2, and at its distal end 20.

The support 3 comprises at its proximal end 19 means 21 for, for example definitive, fixing to the syringe 2. In the example represented, these fixing means take the form of a washer 21 comprising a transverse platform 22 and a rim 23 running in the proximal direction and able to deform and to clip, in particular definitively, onto the collar 8 of the syringe 2. As shown in FIGS. 1 and 16, the rim 23 can also be able to clip onto a ring 12 with plunger anti-withdrawal effect, itself fixed to the collar 8 of the syringe 2, as will be described hereinafter with regard to FIGS. 4 and 5.

The support 3 comprises at its distal end 20 at least one means 24 for preventing the connecting of a parenteral injection member to the tip 44 of the syringe 2. In FIG. 3, this means for preventing the connecting of a parenteral injection member to the tip 44 of the syringe 2 takes the form of a distal part 24 situated at the distal end 20 of the support, the free end 26 of the said distal part 24 exhibiting an axial opening 25 whose internal diameter D, as represented in FIG. 6, is strictly less than that of the external diameter of a base of a parenteral injection member. In this figure, this distal part 24 is a hollow tapered portion converging in the distal direction.

In FIGS. 1 and 16, the support 3 is fixed to the syringe 2 by clipping. In particular, the support 3 is clipped to a ring 12 with plunger anti-withdrawal effect, itself fixed to the syringe 2, as shown in FIG. 4.

In variants that are not represented, the support 3 may be fixed to the syringe 2 by bonding, welding, snap-fastening, crimping or hot deformation.

Represented in FIG. 4 is a syringe 2 suitable for the device according to the invention whose body 4 is furnished on its external surface with an annular piece 12. In the example represented, this annular piece 12 is a ring with plunger anti-withdrawal effect.

Referring to FIG. 5, this ring 12 comprises in a conventional manner a distal platform 13 comprising a semicircular opening 14 corresponding to the dimensions of the tubular body 4 of the syringe 2. The ring 12 also comprises a proximal platform 15 comprising a semicircular opening 16 corresponding to the dimensions of the sliding part of the plunger rod 6 of the syringe 2. The space 17 delimited between the two platforms 13 and 15 is intended to receive the collar 8 of the syringe 2.

Thus, when the ring 12 is clipped to the collar 8 of the syringe 2, as represented in FIG. 4, on account of the particular dimension of the semicircular opening 16 of the lower platform 15, it is impossible to withdraw the plunger from the syringe 2, said plunger being blocked by the ring 12.

Represented in FIG. 6 is the axial opening 25 of the tapered portion 24 of the support 3. In this figure, the perimeter of the opening 25 comprises two notches 27 intended to allow the connecting, for example by a bayonet system, of the tip 44 of the syringe 2 to a particular transfer system attached to the bottle comprising an active principle in powder form for example, system described in FIGS. 17 and 18. In a non represented embodiment of the invention, the opening 25 may comprise only one notch 27 or on the contrary more than two notches 27 able to cooperate with one or several lugs 57 (cf. FIG. 17).

The internal diameter D is the diameter of the circle inscribed within the cross section of the axial opening 25.

This internal diameter is strictly less than the external diameter of a base of a parenteral injection member.

Represented in FIG. 7 is a variant of the support 3 of a device according to the invention, for which the body 18 of the support 3 comprises at least one longitudinal window so as to allow observation of the contents of the syringe 2. In the example represented, the body 18 comprises two longitudinal windows 28. The body 18 comprises at its proximal end 19 an annular rim 29 to which a ring 48 (FIG. 8) with plunger anti-withdrawal effect and matched to the dimensions of the body 18 of the support 3 can be clipped. The body 18 of the support 3 comprises at its distal end 20 a distal part 30, which is a hollow cylinder, and whose opening 31 exhibits an internal diameter strictly less than that of the external diameter of the base of a parenteral injection member.

This cylindrical extreme part 30 comprises at least one exterior lug 45 intended to come into cooperation with a particular transfer system (not represented) linked to a bottle containing an active principle for example. In a variant of the invention that is not represented, the exterior lug 45 is replaced with a threaded part intended to come into cooperation with the transfer system.

Represented in FIG. 8 is a variant of the device 1 according to the invention, in which the support 3 is furnished at its proximal end 19 with a ring 48 with plunger anti-withdrawal effect. This ring 48 with plunger anti-withdrawal effect is similar to the ring 12 with plunger anti-withdrawal effect already described in FIG. 5 but, in this case, the dimensions of the semicircular opening of the distal platform are matched to the dimensions of the body 18 of the support 3. The ring 48 with plunger anti-withdrawal effect is therefore added once the support 3 has been installed on the syringe 2. This ring 48 thus allows the fixing, in particular definitive, of the support 3 to the syringe 2.

For a better understanding, represented in FIG. 11 is a parenteral injection member in the form of a needle 41 fixed on its base 42, for example of tapered shape. This base 42 comprises in a conventional manner a collar 43. The external diameter of the base 42 is therefore the diameter within which the largest cross section of the collar 43 is inscribed.

As represented in FIG. 12, the support 3 being, in particular definitively, fixed to the syringe 2 and its distal end 20 exhibiting an axial opening 31 whose internal diameter is strictly less than the external diameter of the base 42 of the parenteral injection member 41, that is to say strictly less than the external diameter of the collar 43, it is impossible to connect the parenteral injection member, here the needle 41, to the syringe 2.

Represented in FIGS. 9 and 10 is another variant of the device 1 of the assembly according to the invention in which the support 3 is formed of two longitudinal parts 321, 322 fixed together. In these figures, these two longitudinal parts take the form of two half-shells 321 and 322 of semi-tubular shape that can be clipped together. Each half-shell 321, 322 of the support 3 comprises at its proximal end a half-ring 331, 332 able to be clipped to the half-ring 331, 332 of the other half-shell 321, 322. Clipping means, such as a projection 34 and a recess 35 are provided on each half-ring 331, 332 facing a corresponding recess 35 and a corresponding projection 34 on the other half-ring 331, 332 so as to clip the two half-rings 331, 332 together. The ring 36 thus formed imprisons the collar 8 of the syringe 2, as shown in FIG. 10. This ring 36 can have a plunger anti-withdrawal effect.

Clipping means, such as a projection 37 and a recess 38 are provided on the respective edges 39 of each half-shell 321, 322 facing a corresponding recess 38 and a corresponding projection 37 on the other half-shell 321, 322 so as to clip the two half-shells 321, 322 together. In FIG. 10, the two half-shells 321, 322 are fixed together by clipping. The support 3 thus formed imprisons the syringe 2.

In variants that are not represented, the two half-shells 321, 322 may be fixed together by bonding, welding, snap-fastening, crimping, hot deformation, with the aid of a hinge or through a combination of these means.

Represented in FIGS. 13 and 14 is a variant of the device of the assembly according to the invention, for which the support 3 is furnished at its distal end 20 with a cap 46 linked to the support 3 by breakable bridges 47. These breakable bridges serve as tamper-proofing elements.

Represented in FIG. 15 is a variant of the device of the assembly according to the invention, in which the support 3 is furnished with a transverse skirt 49 preventing the device 1 from penetrating too far into the mouth of the patient. There is thus no risk of injuring the patient.

FIGS. 1, 2, 3, 17, 18 and 19 illustrate in combination an assembly according to the invention for the oral administration of a medicinal product to be reconstituted from an active principle 50 in dry or liquid form and from a diluent 11. This assembly comprises the device 1 of FIGS. 1 to 3, in which the syringe 2 is prefilled with the diluent 11, a bottle 51 comprising the active principle 50, in dry form in the example represented, and a transfer system 52 for transferring the diluent 11 to the active principle 50, then the reconstituted medicinal product from the bottle 51 to the syringe 2. The active principle 50 may be in powder or lyophilisate form. The bottle 51 comprises a neck 60 comprising a simple rim 58. The bottle 51 is plugged by a stopper 59 generally held in place by an aluminium crimped ring (not represented) furnished with a foil that can be removed or pierced at the time of use of the bottle 51 with the transfer system 52. The transfer system 52 is separate from the support 3. This transfer system 52 comprises at its distal end 53 a hollow bottom 54 of tapered shape flaring out in the distal direction. This bottom 54 comprises a rib on its interior face intended to clip under the rim 58 of the neck 60 of the bottle 51.

The transfer system 52 comprises at its proximal end 55 an extreme part 56, in the shape of a tapered portion in the example represented, able to connect to the tip 44 of the syringe 2 once the support 3 has been fixed to the said syringe 2. The extreme part 56 of the transfer system 52 comprises means 57 for making safe the transfer system 52 on the device 1. In FIG. 17, these means 57 for making safe take the form of two lugs 57 able to cooperate with the notches 27 of the distal part 24 of the support 3 as represented in FIG. 6.

As represented in FIGS. 20 and 21, these two lugs 57 may be offset in the axial direction (FIG. 20) or in an angular manner (FIG. 21) or else according to a combination of these two modes.

Thus, to reconstitute a medicinal product on the basis of the assembly according to the invention, the user fixes the neck 60 of the bottle 51 onto the bottom 54 of the transfer system 52 by clipping the rim 58 of the neck 60 onto the rib situated on the interior face of the bottom 54 of the transfer system 52. He then connects the transfer system 52, to which the bottle 51 is fixed as represented in FIG. 19, to the tip 44 of the syringe 2 installed in the support 3, by virtue of the extreme part 56 of the said transfer system 52. The transfer system 52 is then made safe on the device 1 by virtue of the cooperation of the lugs 57 of the extreme part 56 of the system and of the notches 27 of the opening of the distal part 24 of the support 3. The diluent 11 of the syringe 2 is then transferred into the bottle 51 where it mixes with the active principle 50 in dry form (or in liquid form), reconstituting the medicinal product which is then sucked back from the bottle 51 into the syringe 2. The transfer system 52 is then disconnected from the device 1. Because the transfer system 52 is separate from the support 3, the support remains firmly fixed to the syringe 2. By virtue of the distal part 24 of the support 3, the connecting of the tip of the syringe 2 with a parenteral injection member is impossible. Moreover, the syringe 2 is perfectly covered by the support 3 surrounding it. It therefore can not enter in contact with the mouth or the body of the patient. It is also protected by the support 3 from breakage risks that may be caused by collisions. The medicinal product can thus be administered to the patient orally without risk, even if the syringe is made out of glass.

Represented in FIG. 22 is a transfer system 52 crimped definitively to the bottle 51. There is thus no risk of the user connecting the transfer system 52 to a bottle comprising a product other than the active principle 50 that one wishes to mix with the diluent 11 present in the syringe.

The assembly according to the invention has the advantage of allowing the use of prefilled syringes, for example standard prefilled syringes made out of glass, for oral administration of product without any risk of wound through contact of the syringe body made out of glass and body parts of the patient and without any risk of the product contained in the syringe being administered parenterally, this being so throughout the syringe handling time.

The present invention is not limited to the forms of execution described in the present patent application by way of example.

The invention claimed is:

1. Assembly for oral administration of a medicinal product to be reconstituted from an active principle in dry or liquid form and from a diluent, comprising:
   i) a device comprising:
      a prefilled syringe with said diluent, furnished at its distal end with a tip and at its proximal end with a collar, this syringe being able by itself to receive a parenteral injection member, the parenteral injection member capable of being coupled to the syringe and having a base with an external diameter
      a support comprising:
         a body of elongate form fastened to the syringe and surrounding it, the support being open at its distal end and at its proximal end, the support comprising at its proximal end means for fixing to the syringe, and, at its distal end, at least one means for preventing the connecting of the parenteral injection member to the tip of the syringe, the preventing means having an opening with a dimension less than the external diameter of the base of the parenteral injection member, so that the support can only be fastened to the prefilled syringe when the parenteral injection member is not received on the prefilled syringe, and whereby the parenteral injection member cannot be attached to the prefilled syringe while the support remains attached to the prefilled syringe;
   ii) a container comprising the active principle in dry or liquid form; and
   iii) a system for transferring the diluent to the active principle, then the reconstituted medicinal product from the container to the syringe, said transfer system being separate from the support,
   wherein the support is fastened to the prefilled syringe before and during the transfer of the diluent to the active principle.

2. Assembly according to claim 1, wherein the support is fixed to the syringe.

3. Assembly according to claim 1, wherein the support is fixed to the syringe by bonding, welding, clipping, snap-fastening, crimping or hot deformation.

4. Assembly according to claim 1, wherein the means for fixing the support to the syringe take the form of a washer comprising a transverse platform and a rim running in the proximal direction and able to deform and to clip to the collar of the syringe.

5. Assembly according to claim 1, wherein the means for preventing the connecting of the parenteral injection member to the tip of the syringe take the form of a distal part, situated at the distal end of the support, the free end of the distal part exhibiting an opening, preferably axial, whose internal diameter is strictly less than the external diameter of the base of the parenteral injection member.

6. Assembly according to claim 5, wherein the internal diameter is less than or equal to 7.70 mm.

7. Assembly according to claim 5, wherein the distance between the longitudinal axis of the tip of the syringe and the point of the perimeter of the opening closest to this axis is less than or equal to 3.85 mm.

8. Assembly according to claim 5, wherein the distal part is a hollow tapered portion converging in the distal direction.

9. Assembly according to claim 5, wherein the distal part is a hollow cylinder.

10. Assembly according to claim 1, wherein the body of the syringe is furnished on its external surface with an annular piece onto which the support is fixed.

11. Assembly according to claim 10, wherein the annular piece is a ring with plunger anti-withdrawal effect.

12. Assembly according to claim 1, wherein the support is formed of two longitudinal parts fixed together.

13. Assembly according to claim 12, wherein the two longitudinal parts are fixed together by bonding, welding, clipping, snap-fastening, crimping or hot deformation, with the aid of a hinge or through a combination of these means.

14. Assembly according to claim 1, wherein the support is furnished at its distal end with a cap linked to the support by at least one breakable bridge.

15. Assembly according to claim 1, wherein the support is furnished with a transverse skirt preventing the device from penetrating too far into the mouth of the patient.

16. Assembly according to claim 1, wherein the body of the support comprises at least one longitudinal window.

17. Assembly according to claim 1, wherein the support is furnished at its proximal end with a ring with plunger anti-withdrawal effect.

18. Assembly according to claim 1, wherein the syringe is made of glass.

19. Assembly according to claim 1, wherein the transfer system comprises at its proximal end an extreme part able to connect to the tip of the syringe once the support has been fixed to the syringe.

20. Assembly according to claim 1, wherein an extreme part of the transfer system comprises means for making safe the transfer system on the device.

21. Assembly according to claim 20, wherein the means for preventing the connecting of the parenteral injection member to the tip of the syringe take the form of a distal part, situated at the distal end of the support, the free end of the distal part exhibiting an axial opening comprising at least one notch, a securing means of the transfer system taking the form of at least one lug, able to cooperate with the notches of the distal part of the support.

22. Assembly according to claim 21, wherein the axial opening comprises two notches and the securing means take the form of two lugs, these two lugs being offset in the axial direction or in an angular manner or else according to a combination of these two modes.

23. Assembly according to claim 1, wherein the transfer system is definitively crimped to the container.

* * * * *